United States Patent [19]

Roberts

[11] 4,267,271

[45] May 12, 1981

[54] RADIOIMMUNOASSAY FOR ISOENZYMES OF CREATIVE KINASE HAVING A B-SUBUNIT AND REAGENTS THEREFOR

[75] Inventor: Robert Roberts, Chesterfield, Mo.

[73] Assignee: Washington University, St. Louis, Mo.

[21] Appl. No.: 62,777

[22] Filed: Aug. 1, 1979

Related U.S. Application Data

[63] Continuation-in-part of Ser. No. 846,095, Oct. 27, 1977.

[51] Int. Cl.³ .............................................. C12Q 1/66
[52] U.S. Cl. ...................................... 435/7; 23/230 B; 424/1; 424/1.5; 424/12; 424/85; 435/188
[58] Field of Search .................. 435/7, 188; 23/230 B; 424/1, 1.5, 12, 85

[56] References Cited

PUBLICATIONS

Robert Roberts et al., Science, vol. 194, pp. 855–857, 1976.
John B. Armstrong et al., Journal of Biological Chemistry, vol. 252, No. 10, pp. 3105–3111; 1977.

*Primary Examiner*—Robert J. Warden
*Attorney, Agent, or Firm*—Grace J. Fishel

[57] ABSTRACT

Methods and materials are disclosed for quantitative detection of isoenzymes of creatine kinase having a B-subunit by radioimmunoassay competitive displacement techniques with antibodies to human MB CK. The antibodies are specific for MB and BB creatine kinase and have no cross-reactivity with MM creatine kinase. Radioisotopically labelled isoenzymes with of creatine kinase having the same affinity for antibodies raised against human MB CK are also disclosed, which with the aforementioned antibodies provide a highly sensitive radioimmunoassay capable of measuring picomolar amounts of MB CK or BB CK.

14 Claims, 3 Drawing Figures

RADIOIMMUNOASSAY FOR ISOENZYMES OF CREATIVE KINASE HAVING A B-SUBUNIT AND REAGENTS THEREFOR

This application is a continuation-in-part of application Ser. No. 846,095, filed Oct. 27, 1977.

BACKGROUND OF THE INVENTION

The present invention relates generally to methods and materials for quantitative detection of isoenzymes of creatine kinase having a B-subunit by radioimmunoassay techniques.

Creatine kinase is a dimeric molecule that exists in at least three isoenzyme combinations designated MM, MB and BB on the basis of monomer composition, M being the predominant form in muscle and B being the predominant form in brain. Plasma from normal human subjects contains primarily MM, with less than 0.005 international unit (IU) of MB per milliliter and no detectable BB CK. The only human tissue containing appreciable amounts of MB CK is myocardium so that elevated MB CK activity in plasma is a remarkably sensitive and specific marker indicator of myocardial injury. Similarly, after cerebral infarction, injury or infection, BB CK is released into the blood but only minor amounts appear in the circulation. This may be due to the blood brain barrier or to other factors. Since BB CK does not appear in human plasma after myocardial infarction and MB CK does not appear in brain after cerebral injury, the availability of a sensitive assay for the B-subunit should be useful in detecting and quantifying a myocardial infarction by measuring MB CK in plasma and detecting and quantifying the extent of cerebral injury after brain damage by measuring BB CK.

In the past, MB CK has been assayed in terms of its catalytic activity. Employing a spectrophotometric technique for detecting NADPH developed from creatine kinase—catalyzed formation of ATP through coupled enzyme systems, CK activity is measured before and after an antibody which will bind with MB CK is conjugated with the sample. The results of such prior art assays are directly dependent on several parameters and because of them, in general, enzyme immunoassays have lower sensitivity than radioimmunoassays. For one thing, the MB CK may be variably enzymatically inhibited by the antibody. For another, there is difficulty in distinguishing MM from MB activity because of the high background of MM CK activity inasmuch as MB CK never makes up more than 10 to 15 percent of total CK activity in plasma, even after acute myocardial infarction. The results also depend on the rate of disappearance of MB activity from plasma. Unfortunately, the factors responsible for disappearance of MB activity from the circulation have not been well elucidated. It is unclear, for example, whether disappearance of enzyme activity is rate limited by inactivation, denaturation or by removal of intact enzyme molecules from circulation. Similar problems are encountered in assaying BB CK by enzyme immunoassay.

The prior art provides certain proposals for radioimmunoassay ("RIA") analysis of plasma samples for use in quantitative detection of enzymes, and specifically creatine kinase isoenzymes, independently of analysis of enzyme activity. See, generally, the review article, "The Measurement of Enzymes by Radioimmunoassay" By J. Landon, et al. [*Ann. Clin. Biochem.*, 14, pp. 90–99 (1977)] which recounts the relative superiority of RIA techniques to those based on catalytic activity. Simply put, according to one such RIA technique a stoichiometric excess of a pure, labelled (radioisotopic) material is allowed to associate (e.g., by antigen/antibody reaction) with the selected reactive substance such as antibody previously exposed to a sample containing an "unknown" quantity of enzyme which is unlabelled, but which is capable of a similar association. Direct quantitative information concerning the "unknown" concentration, as opposed to measuring enzymatic activity, is obtained on the basis of a count of radioactivity of the remaining selected substance which associates with the labelled material.

Nicholson et al., [*Proc. Austral. Assoc. Neurologists*, Vol. 10, pp. 105–108 (1973)] described a method involving labelling skeletal muscle MM creatine kinase with $^{125}I$ and reported development of an RIA for the MM isoenzyme which assertedly measures "enzymes independently of the integrity of the active site." The method employed by Nicholson, et al. for labelling human creatine kinase is that described by Hunter, et al. [*Nature*, Vol. 194, pp. 4956 (1962)], employing chloramine-T to directly introduce the desired isotope into tyrosyl and histidyl residues of the enzyme protein chain. This method, however, has been associated with considerable structural changes (i.e., tertiary structure destruction) and loss of MM isoenzyme activity through disruption of the sulfhydryl-group-containing active site. Because the assay is assertedly specific for the M-subunit, it invites cross-reaction with MM CK and MB CK and is thus incapable of distinguishing elevation of serum MB concentration resulting from myocardial infarction from elevation of serum MM concentration resulting from skeletal muscle damage or disease. The chloramine-T reagent used in the labelling procedure of Nicholson, et al. cannot be used for labelling the BB or MB isoenzymes due to their relative lability (instability, vis-a-vis MM) in the presence of highly oxidative sulfhydryl-group-disrupting, reagents as chloramine-T. If the sulfhydryl group is disrupted, labelled antigen may not have quite the same affinity for the MB antiserum as unlabelled antigen. The consequence of this may show up in loss of sensitivity. In sum, the Nicholson, et al. proposal has not provided a useful basis to develop an RIA for BB and MB isoenzymes.

A prior art publication of interest to the background of the invention is Fang, et al. [*Biochem. Biophys. Res. Comm.*, Vol. 65, pp. 413–419 (1975)] which reports that creatine kinase enzyme activity losses from direct iodination by prior art chloramine-T, thallic trichloride and lactoperoxidase methods may be avoided through use, for iodination, of a Bolton-Hunter acylation reagent which conjugates (combines) at a free amino ($NH_2$) group of the protein, thus avoiding disruption of the active site. The reagent involved was an iodinated compound derived from N-succinimidyl-3-(4-hydroxyphenyl propionate). Fang, et al. labelled rabbit skeletal muscle MM CK. There is no mention of human MM CK nor was there any mention of animal or human MB or BB CK isoenzymes. While the reported preservation of enzyme active sites would have suggested that a more accurate RIA for MM creatine kinase than that of Nicholson, et al. might be secured, the prior art was still without a method for labelling the more labile MB and BB CK isoenzymes. Furthermore, the antibody noted in Fang, et al. was to rabbit MM CK which offered no specificity for human BB or MB CK isoenzymes. The necessary ingredients for a human CK isoenzyme RIA with a specific antibody to BB and MB CK and the necessary stabilizing conditions for such analysis were yet to be developed.

The radioimmunoassay described and claimed in the aforementioned application Ser. No. 846,095 was performed with antiserum to BB CK. In this assay, $^{125}$I-BB CK binding to BB antiserum was inhibited by unlabelled MB CK and formed the basis for measuring unknown amounts of MB CK in plasma. The specificity of MB CK antiserum for the B-subunit was also disclosed. While it would have been preferred to use $^{125}$I-MB CK and MB CK antiserum in a radioimmunoassay for MB CK, this was not feasible at that time since there was no method for complete purification of MB CK. The chief contaminant in MB CK is albumin which has a similar isoelectric point to MB CK and co-precipitates with it. Whereas impure MB CK could be used to displace binding of $^{125}$I-BB to BB antiserum, impure MB CK labelled with $^{125}$I could not be used since counts would also be on the albumin and would not be displaced with MB CK.

In the present application, a method for the purification of MB CK is disclosed. Purified MB CK is then radioisotopically labelled and a radioimmunoassay described and claimed with antiserum to MB CK. This assay has several advantages over the assay based on BB antiserum. MB CK is more stable than BB CK when labelled and has a longer shelf life making it more appropriate for routine clinical analysis. The assay also has greater reproducibility in that MB binding to MB antiserum is being displaced with MB rather than displacing BB binding to BB antiserum with MB CK. However, if purified MB is used with the BB system as described and claimed in Ser. No. 846,095, sensitivity and reproducibility are still adequate for diagnostic purposes.

BRIEF SUMMARY

The present invention provides methods and materials for accurate and extremely sensitive analysis, by RIA with antiserum to MB CK, of B-subunit-containing isoenzymes of creatine kinase and therefore permits, for the first time, the accurate determination of serum MB CK without either reliance upon kinase activity (ATP and then NADPH formation) or substantial interference by the MM isoenzyme as well as the accurate determination of tissue or blood BB CK. As such, the invention is expected to provide a most useful tool for the early diagnosis of myocardial infarction and for disorders which may involve release of BB CK.

According to the invention, antibodies to human MB CK are obtained by immunization of rabbits with purified MB CK to provide serum containing antibodies which demonstrate specificity for BB and MB isoenzymes, but no cross-reactivity with the MM isoenzyme. Pure MB CK from myocardial tissue and/or BB CK from brain tissue is labelled with $^{125}$I in such a way that its affinity for antibodies to MB CK is substantially the same as the unlabelled isoenzyme. This is accomplished by means of a radioisotopically labelled carrier molecule which is attached to the MB CK or BB CK under reducing conditions such that the sulfhydryl groups are not oxidized, said groups being present in both the M and B-subunits. One suitable means for labelling the isoenzymes with a labelled carrier molecule is through the use of a Bolton-Hunter acylating agent [e.g., N-succinimidyl-3-(4-hydroxyphenyl propionate)].

Incubation of MB CK antibody with labelled and unlabelled isoenzyme is preferably carried out in an aqueous solution wherein the ionic strength and buffer pH has a combined effect selected to preserve active site and tertiary structure by controlling the electrostatic interaction between antibody and antigen. Said ionic strength and buffer pH further selected to retard undesirable "polymerization" caused by multiple reactions between antigen and antibody moieties, dissociation of reacted moieties and nonspecific binding. The proper ionic strength and buffer pH were arrived at empirically and would not necessarily have been predicted.

Incubation is preferably carried out in an aqueous buffer comprising Tris at a concentration of from about 1.2 to about 2.0 M, and preferably 1.6 M, having a pH of from about 7.0 to about 8.0 and preferably 7.4. A preferred buffer also includes a suitable organic reducing agent such as mercaptoethanol in a concentration of from about 5.0 to about 30.0 mM to retard oxidation of the aforementioned sulfhydryl groups, and preferably 20.0 mM, as well as standard agents such as gamma globulin and serum albumin for the prevention of nonspecific binding. Separation of unbound (unreacted) reactants can be performed by using ammonium sulfate but the double-antibody method as described in the examples is preferred because it permits a more rapid assay with incubation periods as short as 30 minutes.

For purposes of indicating the background and/or illustrating the state of the art pertaining to the invention, applicant specifically incorporates by reference herein the disclosures of his jointly-authored publication entitled "Radioimmunoassay for Creatine Kinase Isoenzymes" appearing in *Science*, Vol. 194, pp. 855–857 (November, 1976) as well as the disclosures of the above-mentioned Landon, et al. article.

Further aspects and advantages of the present invention will become apparent upon consideration of the following detailed description and drawing wherein:

FIG. 1 graphically represents analytical findings concerning specificity of MB antibodies;

FIG. 2 graphically represents concentration-dependent competitive displacement of $^{125}$I labelled MB CK by unlabelled isoenzyme; and FIG. 3 graphically compares results of practice of the invention to prior art practices.

DETAILED DESCRIPTION

Figure 1:
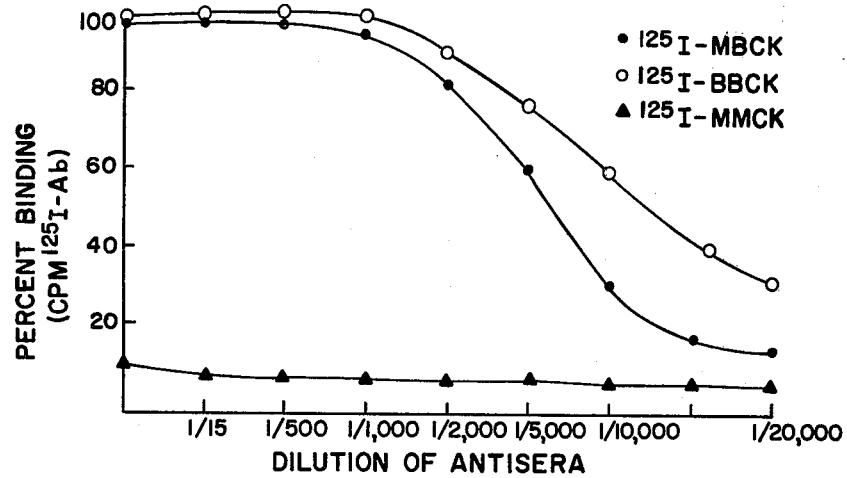

The following Examples illustrate practice of the invention and more specifically relate to (a) isolation of purified human CK enzymes for use in providing labelled enzymes; (b) labelling of CK isoenzymes; (c) preparation of antibodies to MB CK; (d) analysis of binding affinity and specificity of the antibodies; (e) general RIA procedures; (f) determination of MB CK in a plasma sample; and (g) methods and material for a typical clinical analysis for MB CK in a plasma sample.

EXAMPLE 1

Isolation of Purified Human CK Isoenzymes

MM and MB isoenzymes were prepared from human myocardium and BB from human brain obtained at necropsy within six hours of death. Homogenates from human myocardium and brain were prepared as follows. The fresh tissue was trimmed of fat, cut into small pieces with scissors and passed through a pre-cooled meat grinder. Ground tissue was homogenized in a Wilem Polytron or Waring blender containing 50 mM Tris-HCl [Tris (hydroxymethyl) aminoethane hydrochloride], pH 7.4, and 0.002 M 2-mercaptoethanol (Buffer A). All preparative procedures were performed at 0°–4° C.

The myocardial homogenate was centrifuged at 31,000 g for 15 minutes and the supernatant fraction filtered through 8 layers of cheesecloth. Ninety-five percent ethanol was added to the supernatant in dropwise fashion until the final concentration was 50%, and the mixture was allowed to stand while slowly stirred at 4° C. for 30 minutes. The precipitated material was removed by centrifugation and the supernatant fraction decanted. Again ethanol was added in stepwise fashion until a final concentration of 70% was obtained. The mixture was allowed to stand for 30 minutes and the resulting precipitate was recovered and saved. With the use of a homogenizer, the precipitated pellet was suspended in homogenizing medium equal in volume to 50% of the original homogenate. After centrifugation at 31,000 g, the pellet from this resuspended mixture was discarded and the supernatant fraction dialyzed for 1 hour in 50 mM Tris-HCl, pH 8.0, and 2 mM BME [barbital 2-mercaptoethanol] (Buffer B) and applied to a DEAE-A50 Sephadex column equilibrated with Buffer B. After 50 ml of Buffer B had been collected, elution was started with a salt gradient (50–500 mM NaCl). Fractions were collected and analyzed for MM and MB CK activity and shown to be separated with MM being eluted first and MB CK being in the second peak.

The fractions from the first peak containing MM CK were further purified by dialysis against Tris-barbitol, pH 6.0 and 5 mM BME (Buffer C). Following dialysis, the MM CK was further purified on CM Sephadex using Buffer C for elution and a pH gradient of 6.0–8.0. The fractions with MM CK activity were pooled and dialyzed in 50 mM Tris-HCl, pH 7.4, and 5 mM BME and then concentrated by Amicon filtration using a UM-10 filter.

The fractions containing MB CK were pooled and shown to contain a large amount of albumin as a contaminant along with other unidentified contaminating proteins. The MB CK was separated from the contaminants by column chromatography using Affi-gel Blue (100–200 mesh, Bio-rad) which had previously been equilibrated with Buffer B. The MB CK was eluted with NaCl (250 mM) leaving the albumin and other proteins adsorbed to the column. The MB CK fraction was recovered and concentrated by Amicon filtration using a UM-10 filter.

CK was extracted from brain in the same fashion as from myocardium with the following exceptions. The final concentration of ethanol was 60% rather than 50%. After filtration to remove any potential MM fraction, the fraction with BB CK was applied to a DEAE-A50 Sephadex column and was eluted with Tris-HCl buffer, pH 8.5, with 0.3 M NaCl.

Polyacrylamide gel electrophoresis [per Anido, et al., Am. J. Clin. Path., Vol. 61, p. 599 (1974)] of the human preparations indicated that each isoenzyme was obtained in a simple devoid of activity attributable to other isoenzymes in the initial extract. MM CK averaged 425 IU/mg of protein, MB 456 IU/mg, and BB 435 IU/mg. Specific activity of the isoenzymes was increased by more than five hundred-fold over that present in the initial extract and analysis by SDS gel electrophoresis [per Weber, et al., J. Biol. Chem., Vol. 244, p. 4406 (1969)] with staining for protein showed only one protein band for MM, one for BB and one for MB, indicating that the preparations were probably 99% pure.

EXAMPLE 2

Radioactive Labelling of CK Isoenzymes

Radioiodine ($^{125}I$) was utilized to radioactively label CK isoenzymes for subsequent use in a competitive displacement radioimmunoassay. To avoid exposing the enzymes to oxidizing agents and contaminants in the radioiodine, the $^{125}I$ was first incorporated into N-succinimidyl ester 3-(4-hydroxyphenyl propionate) which in turn was reacted with amino groups on the CK isoenzyme protein. Radioiodination was performed by the method of Bolton and Hunter, supra, carried out at room temperature (23° C.). N-succinimidyl 3-(4-hydroxyphenyl propionate) (0.3 mcg) was treated with 5 millicuries (10–20 ul) of $Na^{125}I$, 50 mcg of chloramine-T and 10 ul of 0.25 M phosphate buffer, pH 7.5. The reaction was immediately terminated by the addition of 120 mcg of sodium metabisulfite in 10 ul of 0.50 M phosphate buffer, pH 7.5 containing 200 mcg of KI. The iodinated product was extracted into benzene (0.300 ml×2 portions) and recovered by evaporation of the solvent under vacuum. The addition of dimethylformamide (5 ul) before adding the benzene was necessary for full extraction of the ester into the solvent. The residue was used to label CK isoenzymes. The labelled residue was combined with 2–8 mcg of MM, MB or BB CK in 1–2 ml of 0.01 M Na-borate buffer, pH 8.5. After gently shaking the reaction, for four hours at 4° C., the labelled isoenzymes were then dialyzed against the same buffer containing 0.005 M 2-mercaptoethanol. Radioactivity per mcg of labelled CK isoenzymes ranged from 5–25 uCi for MM CK, MB CK and BB CK. The maximum loss of enzyme activity resulting from labelling and dialysis was less than 5% for each isoenzyme preparation.

EXAMPLE 3

Preparation of Antibodies to CK Isoenzymes

Utilizing the purified human MM, MB and BB CK mixed with equal volumes of Freund's complete adjuvant, antibodies to CK isoenzymes were induced in rabbits. Initially, the rabbits were injected subcutaneously with 1 mg of immunogen (0.25 mg/foot pad). Subsequently, they were injected with 0.25 mg weekly for three weeks. All animals were given booster injections of 0.1 mg in complete adjuvant at monthly intervals thereafter. Ten days after each booster injection, the animals were bled and their serum analyzed for antibody activity. Ouchterlony agarose plates, prepared with BB and with MB antiserum exhibited single precipitant lines to BB and MB antigen but no precipitant line to MM. Plates prepared with MM antiserum exhibited a single precipitant line to both MB and MM but none to BB. Thus, antibodies to BB CK reacted with BB CK and also cross-reacted with MB but did not cross-react with MM indicating that it was specific for the B-subunit. Antibodies to MB CK reacted with MB CK and also cross-reacted with BB but did not cross-react with MM indicating that they are also specific for the B-subunit and antibodies to MM, on the other hand, were specific for the M-subunit.

EXAMPLE 4

Binding Affinity and Specificity of Antiserum

The binding affinity and specificity of the BB, MB and MM antibodies (rabbit antiserum of Example 3) was determined over a wide range of concentrations of the antibody by diluting the appropriate antiserum over a range of 1:15 to 1:1000. All determinations performed in duplicate were carried out in 12×75 mm glass tubes containing 1.6 M Tris buffer, pH 7.6 (200 ul), 2% bovine serum albumin (100 ul), 0.020 M mercaptoethanol (10 ul), 5 picograms of rabbit gamma globulin (50 ul). As noted earlier, the gamma globulin and serum albumin are believed to minimize nonspecific binding and the high concentration of Tris and 2-mercaptoethanol is believed to protect the sulfhydryl groups of the isoenzymes and prevent dissociation into monomers. To this mixture was added the appropriate dilution of antiserum in volumes ranging from 100 ul to 5 ul (dilutions performed with normal rabbit serum). $^{125}$I-labelled MM (1ng), MB (1ng), and BB CK (1ng) were added such that approximately 25,000 cpm were present in each tube. The total volume was kept constant at 500 ul with necessary adjustments being made with Tris buffer. The solutions were then incubated and gently shaken at 4° C. for six hours. Appropriate controls were incubated containing normal rabbit serum rather than rabbit antiserum.

Following the incubation period, separation of free from antibody bound labelled CK was accomplished by the addition of a second antibody which is raised to rabbit gamma globulin in sheep or goats. The solution is allowed to sit at room temperature for 15 minutes and is then centrifuged at 2,000 g for 20 minutes, the supernatant decanted, and the pellet counted in a gamma counter (Micromedic Systems, Inc.) until a minimum of 10,000 counts were obtained. The $^{125}$I counts present in the pellet expressed as a percent of the total number of counts initially present represent percent binding. To optimize conditions for any possible cross-reactivity between the MB antibody and MM CK and vice versa for the MM antibody with BB CK, determinations were done in which MB antiserum diluted only 1:15 was incubated with 0.1–4 mcg of $^{125}$I MM. The MM antiserum in a dilution of 1:15 was incubated with 0.1–4 mcg. of $^{125}$I BB.

Results of binding experiments using serial dilutions of MB antiserum from 1:15 to 1:1000 incubated with iodinated MM, MB and BB CK were obtained. Ninety-seven percent of the $^{125}$I BB was recovered in the pellet in dilutions of 1:15, but binding diminished rapidly with only 16% at 1:15,000, demonstrating that binding was dependent on antibody concentration. Maximum binding of $^{125}$I MB CK occurred at 1:15 dilutions but again binding was dependent on the concentration of antibody with 25% binding at 1:20,000 dilution. In contradistinction, $^{125}$I MM exhibited no such antibody concentration dependent binding and at all dependent binding and at all dilutions was the same being between 3–10% which is the same as that of control (normal rabbit serum). These results demonstrated the antibody is specific for the B-subunit rather than the molecule as a whole.

EXAMPLE 5

General Procedure for Radioimmunoassay

To develop a competitive displacement radioimmunoassay for plasma MB CK, MB antiserum was used and the specificity of the MB antiserum for B-subunits further established by comparing the ability of unlabelled BB, MB and MM CK to inhibit $^{125}$I MB binding. The reaction was performed in the same buffer solution used for the binding experiments, but with the exceptions that the dilution of antiserum was kept constant at 1:5000 and the amount of $^{125}$I MB CK was kept constant at 1ng containing approximately 25,000 cpm. The antiserum dilution of 1:5000 was chosen since this concentration of antibody binds about 60% of the $^{125}$I MB [See generally, Parker, C. W., "Radioimmunoassays" in *Progress in Clinical Pathology*, Volume IV (Grune and Stratton, Inc., New York, 1974)]. A known amount of unlabelled BB, MB or MM CK was incubated for 15 minutes with $^{125}$I-labelled MB. Following incubation, the precipitated pellet was washed, centrifuged and counted for $^{125}$I radioactivity. To further determine the specificity of unlabelled BB or MB to displace $^{125}$I MB binding in the face of MM CK, inhibition curves were determined for MM incubated with BB or MB in which MM was present in a 25,000-fold excess over that of unlabelled BB or MB.

Figure 2:
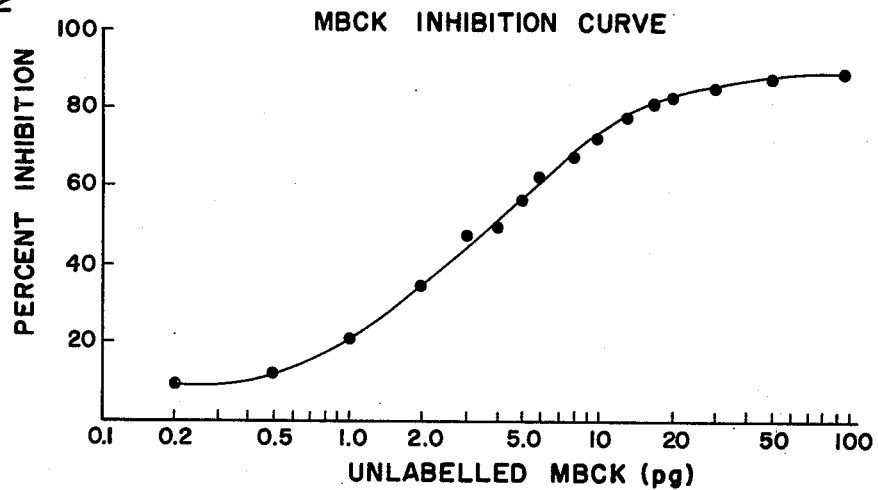

Unlabelled MB CK competitively displaced labelled MB CK from binding to the MB antibody which was dependent on the concentration of MB CK as shown in FIG. 2. The inhibition curve is steep between 0.5–20 pg/ml with 50% inhibition at 4 pg and complete inhibition of binding at a concentration of 30 pg/ml and above. A similar inhibition curve was seen for unlabelled BB which showed 50% inhibition at 60 pg/ml and complete inhibition at 125 pg/ml and higher. Unlabelled MM CK showed no inhibition of $^{125}$I binding, even at 5 mcg/ml (2000-fold excess over $^{125}$I MB CK). Furthermore, the competitive inhibition of unlabelled MB CK was unaltered in the presence of high concentrations of MM CK (5000 M excess over that of MB CK). Thus, the MB system as a competitive displacement assay for MB is extremely sensitive, detecting reliably a concentration of 2 pg/ml which in terms of enzymatic activity is $1\times10^{-7}$ IU/ml. Furthermore, the specificity is such that it detects at this level of sensitivity even in the presence of a 5000 molar excess of MM. Results of radioimmunoassays performed on heat inactivated serum constituted with known amounts of MB CK ranging from 20 pg/ml to 2 mcg/ml deviated by less than 3% from that expected.

EXAMPLE 6

Determination of MB CK in Plasma Samples

To determine the amount of MB CK present in an unknown sample, a standard MB inhibition curve is run with known amounts of unlabelled MB CK ranging from 2,000 to 20 picograms pg/ml of MB CK. The unlabelled MB CK is incubated with a constant amount of MB antiserum and $^{125}$I MB CK as outlined previously under radioimmunoassay procedure. Serial dilutions (3–4) of the unknown sample are made and the amount of inhibition determined at each dilution and compared to the standard curve from which it is possible to calculate the amount of MB CK present expressed as ng/ml. To determine the accuracy of the assay, known amounts of human unlabelled MB CK were added to heat inactivated serum and serial dilutions done and results expected compared to that obtained. Plasma samples were obtained from five patients with acute myocardial infarction. At least 15 samples were obtained serially from each patient over a period of 48 hours. All samples were performed in duplicate and compared to enzymatic activity obtained by a kinetic fluorometric assay previously described in Roberts, et al., *Am. J. Cardiol.*, Vol. 33, p. 650 (1974). All determinations for total CK enzymatic activity were done according to the method of Rosalki, S. B., *J. Lab. Clin. Med.*, Vol. 62, P. 696 (1967).

Figure 3:
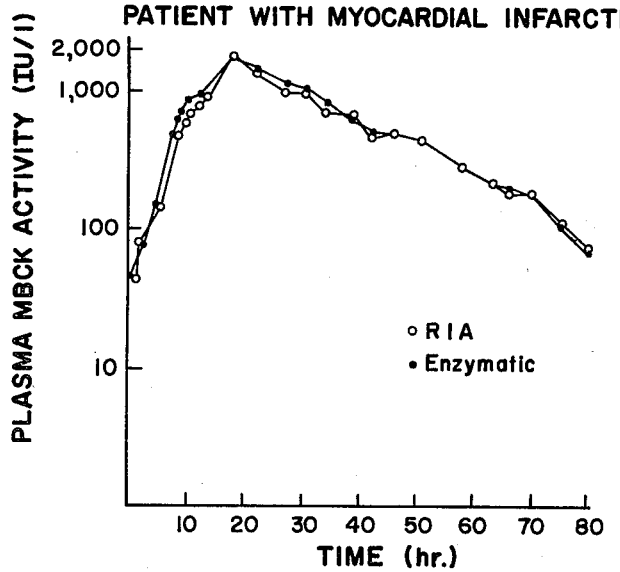

Results of samples obtained from five patients with acute myocardial infarction exhibited elevated MB CK in all cases. A typical MB CK curve from one of the patients is shown in FIG. 3 and demonstrates a high degree of correlation between activity-related and RIA analysis findings for a situation wherein the MB CK level is markedly elevated.

EXAMPLE 7

Typical Clinical Analysis for MB CK in a Plasma Sample

A. Materials

1. Five (5) vials, A-1, A-2, A-3, A-4 and A-5, are prepared with each containing the same known amount of $^{125}$I-labelled human MB CK.

2. Four (4) vials marked B-1, B-2, etc., are prepared with each containing unlabelled human MB CK with known amounts such that there would be a 100%, 60%, 40% and 20% inhibition of binding respectively (used to obtain the control standard inhibition curve).

3. Five (5) vials marked C-1, C-2, etc., are prepared with each containing the same known amount of human MB antiserum.

4. Six (6) vials marked D-1, D-2, etc., are prepared with each containing the same known amount of RIA-buffer (400 ul) containing 1.6 M Tris, 20 mM mercaptoethanol or other suitable reducing agent, 5 pg of rabbit gamma globulin and 0.05% of bovine serum albumin at a pH of 7.4.

B. Methods

1. Vials C-1, C-2, C-3, C-4 are mixed with B-1, B-2, B-3, B-4 vials and D-1, D-2, D-3 and D-4 vials respectively and incubated for 15 minutes with gentle shaking at 4° C. and referred to as AB-1, AB-2, etc.

2. Following the above incubation steps, vials A-1, A-2, A-3, A-4 are added respectively to the appropriate AB vials (1,2,3,4) and incubated for 15 minutes at 4° C. with gentle shaking.

3. Contemporaneously with steps 1 and 2, the C-5 vial is mixed with D-5 and 100 ul of plasma from the unknown sample and incubated for 15 minutes at 4° C. with gentle shaking after which it is added to A-5 vial and incubated for 15 minutes as above.

4. Following the 15 minutes incubation, 100 ul of second antibody is added to all the tubes and incubated with gentle shaking for 15 minutes at 4° C.

5. All the tubes are centrifuged at 2000 g for 20 minutes.

6. Supernatant is discarded from all the tubes and 200 ul of buffer from D-6 tube is added for one washing and again supernatant is discarded.

7. The tubes containing the residue pellets are now put in the gamma counter and counted for radioactivity. The amount of binding present in vials 1-4 are plotted against the amount of CK present in vials marked B-1, B-2, etc. to obtain the standard inhibition reference curve. The amount of binding in the unknown plasma sample is placed on the curve and from the abscissa the amount of MB CK can be determined.

The above Examples have described a radioimmunoassay for CK isoenzymes. Antibodies were developed for MM, MB and BB CK, those raised against MM being specific for the M-subunit while those raised against MB or BB being specific for the B-subunit. Since MB CK, found in the human myocardium, contains both subunits, all three antibodies can be used to detect MB CK. The BB antibody reacts with BB and cross-reacts with MB CK, but not MM even when present in 5,000 molar excess over that of MB CK, a ratio far greater than that seen in plasma after myocardial infarction since MB CK is usually 10-15% of total CK activity. Similarly, the MB antibody reacts with MB and cross-reacts with BB CK, but not with MM even when present in great excess. Detection of plasma MB CK using the BB or MB system is, therefore, specific for MB. Because BB CK activity is not present in normal plasma, even in patients with cerebral disorders or those with acute myocardial infarction, displacement binding reflects MB exclusively. This was corroborated by the close agreement (See, e.g., FIG. 3) between enzymatic activity determined by the kinetic fluorometric method and that obtained by the radioimmunoassay in samples obtained from patients with acute myocardial infarction.

The sensitivity provided by the assay (and illustrated in FIG. 2) is believed to exceed that of any prior assay by several fold. Present assays based on enzymatic activity can barely detect 0.010 IU/ml as opposed to the present assay which detects reliably 0.00001 IU/ml. Since mean plasma MB CK activity is 0.002 IU/ml, a five-fold increase is necessary for detection by enzymatic assays as opposed to the present assay which reliably detects any increase above normal. The increased sensitivity, coupled with its potential for detection of enzymatically inactive MB CK in the circulation should lead to improved estimates in infarct size as well as earlier detection of acute myocardial infarction. This is of particular importance in view of the recent enthusiam for protection of ischemic myocardium in patients with acute myocardial infarction which demands a definitive diagnosis as soon as possible, since agents that can potentially decrease infarct size would be more effective if administered early.

The high level of specificity and sensitivity in the B-subunit-containing CK isoenzyme radioimmunoassay system suggests that a similar approach may be useful in differentiation of other clinically important enzymes which exist in multiple forms. Studies evaluating the disappearance of other enzymes from the circulation have been restricted to determining the loss of activity. Because this assay detects the concentration of molecules, one can determine the actual rate of isoenzyme protein turnover independent of activity.

The assay should also help to elucidate mechanisms responsible for disappearance of individual CK isoenzymes from the circulation as well as aid in elucidating the relative importance of inactivation, denaturation, or removal of CK molecules under various clinical circumstances.

Numerous modifications and variations of the invention are expected to occur to those skilled in the art upon consideration of the foregoing detailed description. It can be anticipated that substantial variation in modes of securing BB CK or MB CK antibodies, in labelling CK isoenzymes and in preparing suitable dissociation and polymerization-retarding buffers will be made. Consequently, only such limitations as appear in the appended claims should be placed upon the invention.

What is claimed is:

1. A competitive displacement radioimmunoassay method for quantitative determination of the concentration of a B subunit-containing isoenzyme of human creatine kinase in a sample, said method comprising:

(1) incubating said sample with a pre-determined stoichiometric excess quantity of antibodies to purified MB creatine kinase to form a first reaction mixture comprising (a) the product of antigen-antibody association of B subunit-containing isoenzymes in the sample with antibodies to purified MB creatine kinase, and (b) unreacted antibodies to purified MB creatine kinase;

(2) incubating the reaction mixture of step (1) with a stoichiometric excess of radioisotopically labelled, purified B subunit-containing isoenzymes of creatine kinase to form a second reaction mixture comprising the association product of step (1) and the product of antigen-antibody association of said labelled isoenzymes with said unreacted antibodies in said first reaction mixture; and (3) removing unreacted labelled isoenzymes from said second reaction mixture and ascertaining the concentration of B subunit-containing isoenzymes in said sample on the basis of the extent of antigen-antibody association between said antibodies and said labelled isoenzyme.

2. The method of claim 1 wherein said antibody to purified MB creatine kinase is isolated from an animal immunized with purified MB creatine kinase.

3. A competitive displacement radioimmunoassay method for quantitative determination of the concentration of a B subunit-containing isoenzyme of human creatine kinase in a sample, said method comprising:

(1) incubating said sample in a medium having reducing agent activity with a pre-determined stoichiometric excess quantity of antibodies to purified MB creatine kinase to form a first reaction mixture comprising (a) the product of antigen-antibody association of B subunit-containing isoenzymes in the sample with antibodies to purified MB creatine kinase, and (b) unreacted antibodies to purified MB creatine kinase;

(2) incubating the reaction mixture of step (1) in a medium having reducing agent activity with a stoichiometric excess of radioisotopically labelled, purified B subunit-containing isoenzymes of creatine kinase to form a second reaction mixture comprising the association product of step (1) and the product of antigen-antibody association of said labelled isoenzymes with said unreacted antibodies in said first reaction mixture, said labelled isoenzymes prepared by attaching a suitable radioisotopically labelled carrier molecule to the isoenzyme thus avoiding exposure of said isoenzyme to oxidative damage during labelling; and (3) removing unreacted labelled isoenzymes from said second reaction mixture and ascertaining the concentration of B subunit-containing isoenzymes in said sample on the basis of the extent of antigen-antibody association between said antibodies and said labelled isoenzyme.

4. The method of claim 3 wherein the medium wherein said incubation steps are carried out retards multiple reactions between antigen and antibody moieties and retards dissociation of the reacted moieties.

5. The method of claim 3 wherein said incubation steps are carried out in an aqueous buffer medium comprising Tris and having a pH of from 7.0 to about 8.0.

6. The method of claim 5 wherein the pH of said buffer is about 7.4.

7. The method of claim 6 wherein said reducing agent is mercaptoethanol.

8. The method of claim 3 wherein the radioisotopically labelled, purified B subunit-containing isoenzyme is an acylation product of the reaction of purified isoenzyme with iodinated N-succinimidyl-3-(4-hydroxyphenyl propionate).

9. The method of claim 8 wherein the medium wherein said incubation steps are carried out is an aqueous buffer having a pH of about 7.4 and comprising Tris, gamma globulin, serum albumin and mercaptoethanol.

10. A combination of reagents for use in the quantitative detection, by radioimmunoassay of the concentration of a B subunit-containing isoenzyme of creatine kinase in a sample, said combination of reagents comprising (1) a pre-determined quantity of an antibody to purified MB creatine kinase, reactive with B subunit-containing isoenzymes of creatine kinase to form an antigen-antibody association upon contact therewith and being substantially unreative with MM creatine kinase; and (2) a pre-determined quantity of a radioisotopically labelled, purified B subunit-containing isoenzyme of creatine kinase, capable of antigen-antibody association with said antibody upon contact therewith, said labelled isoenzymes prepared by attaching a suitable radioisotopically labelled carrier molecule to the isoenzymes thus avoiding exposure of said isoenzyme to oxidative damage.

11. A combination of reagents in claim 10 further including a medium which has reducing agent activity and which retards multiple reactions between the antigen and antibody moieties and which retards dissociation of the reacted moieties.

12. A combination of reagents as set forth in claim 11 wherein the medium is an aqueous buffer solution having a pH of about 7.4 comprising Tris, gamma globulin, serum albumin and mercaptoethanol.

13. A combination of reagents as set forth in claim 11 wherein said radioisotopically labelled, purified isoenzyme is an acylation product of the reaction of purified isoenzyme with iodinated N-succinimidyl-3-(4-hydroxphenyl propionate).

14. A combination of reagents as set forth in claim 13 wherein said radioisotopically labelled, purified isoenzyme is MB isoenzyme.

* * * * *